United States Patent
Lotfi

(10) Patent No.: US 9,597,421 B2
(45) Date of Patent: Mar. 21, 2017

(54) SURFACE MODIFIED DEVICES AND STERILE PACKAGING THEREFOR

(75) Inventor: Atoosa Lotfi, Valencia, CA (US)

(73) Assignee: Advanced Bionics AG, Staefa (CH)

(*) Notice: Subject to any disclaimer, the term of this patent is extended or adjusted under 35 U.S.C. 154(b) by 260 days.

(21) Appl. No.: 14/389,965

(22) PCT Filed: Apr. 3, 2012

(86) PCT No.: PCT/US2012/032018
§ 371 (c)(1),
(2), (4) Date: Oct. 1, 2014

(87) PCT Pub. No.: WO2013/151539
PCT Pub. Date: Oct. 10, 2013

(65) Prior Publication Data
US 2015/0057733 A1     Feb. 26, 2015

(51) Int. Cl.
| | |
|---|---|
| A61L 2/14 | (2006.01) |
| B29C 71/00 | (2006.01) |
| B29C 59/14 | (2006.01) |
| B65B 55/16 | (2006.01) |
| B65B 55/22 | (2006.01) |
| A61N 1/375 | (2006.01) |
| A61N 1/05 | (2006.01) |
| B65B 55/04 | (2006.01) |

(Continued)

(52) U.S. Cl.
CPC .......... *A61L 2/14* (2013.01); *A61N 1/05* (2013.01); *A61N 1/0541* (2013.01); *A61N 1/375* (2013.01); *B29C 59/14* (2013.01); *B29C 71/0009* (2013.01); *B65B 55/04* (2013.01); *B65B 55/16* (2013.01); *B65B 55/18* (2013.01); *B65B 55/22* (2013.01); *A61L 2202/21* (2013.01); *A61L 2400/18* (2013.01); *A61N 1/36032* (2013.01)

(58) Field of Classification Search
CPC  A61L 2/14; B65B 55/04; B65B 55/16; B65B 55/18; B65B 55/22
USPC .............................................. 422/22; 607/137
See application file for complete search history.

(56) References Cited

U.S. PATENT DOCUMENTS

| | | |
|---|---|---|
| 4,122,942 A | 10/1978 | Wolfson |
| 5,755,762 A | 5/1998 | Bush |
| 5,762,185 A | 6/1998 | Dulger |

(Continued)

FOREIGN PATENT DOCUMENTS

WO   2007064594 A2   6/2007

OTHER PUBLICATIONS

Demetri Chrysostomou "Gas Plasma Precision Cleaning, Sterilization and Surface Activation of Orthopedic Implants Promotes Biocompatibility in a Single, Highly Reproducible Process Step." Application Note Series, PVA TePla America, Inc., pp. 1-2, Feb. 2011.

(Continued)

*Primary Examiner* — Sean E Conley
(74) *Attorney, Agent, or Firm* — Fabian VanCott; Steven Nichols

(57) ABSTRACT

A method for sterile packaging of a surface modified implantable device includes irradiating a surface of the device such that the hydrophobicity of the surface is decreased and, optionally, the device is simultaneously sterilized. The surface of the sterile, surface-modified implantable device is then covered in a polar solution to prevent hydrophobic recovery of the surface.

23 Claims, 7 Drawing Sheets

(51) Int. Cl.
*B65B 55/18* (2006.01)
*A61N 1/36* (2006.01)

(56) References Cited

U.S. PATENT DOCUMENTS

| | | |
|---|---|---|
| 6,116,413 A | 9/2000 | Tabor et al. |
| 6,440,366 B1 | 8/2002 | Salpekar et al. |
| 2007/0122540 A1 | 5/2007 | Salamone et al. |
| 2010/0285084 A1* | 11/2010 | Yang ..................... A61L 27/34 |
| | | 424/423 |

OTHER PUBLICATIONS

Ih-Houng Loh "Plasma Surface Modification in Biomedical Application" AST Technical Journal, AST Products, Inc., p. 1-6, Jan. 1999.

* cited by examiner

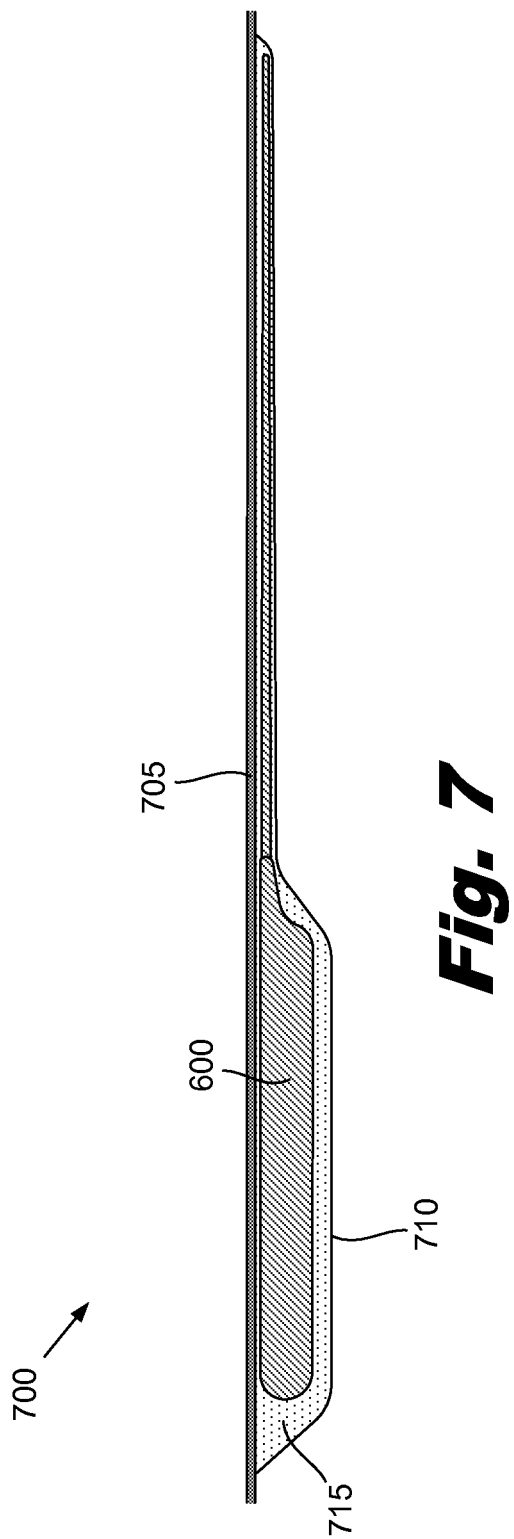

SURFACE MODIFIED DEVICES AND STERILE PACKAGING THEREFOR

BACKGROUND

Manufacturing of medical devices can include a wide variety of processes, including surface modification, sterilization, and packaging. Surface modification refers to techniques that alter the outer surface of an object without substantially altering the bulk properties of material on the interior of the object. Surface modification can provide significant advantages in medical devices by improving the interaction of the medical devices with surrounding biological tissue. However, many types of surface modification are short lasting, with the surface returning to its original condition in a short period of time. Sterilization of medical devices eliminates living bacteria, viruses, and other microorganisms from surfaces and materials. Product packaging of medical devices can serve a variety of purposes including preserving sterilization and physical protection from mechanical shock, electrostatic discharge, compression, and temperature variations.

BRIEF DESCRIPTION OF THE DRAWINGS

The accompanying drawings illustrate various examples of the principles described herein and are a part of the specification. The illustrated examples are merely examples and do not limit the scope of the claims.

FIG. 7 is a cross sectional view of a packaged medical device, according to one example of principles described herein.

Throughout the drawings, identical reference numbers designate similar, but not necessarily identical, elements.

DETAILED DESCRIPTION

The design and manufacture of a medical device for use in the body involves of a number of interrelated processes, including methods for manufacturing the device with the desired characteristics, sterilizing the device, and packaging the device to preserve its characteristics. These processes should be mutually compatible and cost effective. As discussed above, sterilization eliminates pathogens from a medical device and surface modification can be used to alter the outer surface of the medical device to improve its biocompatibility. The product packaging maintains the integrity of the medical device until the device is removed from the packaging and used in the patient.

However, integrating these sterilization, surface modification, and packaging methods in a cost effective manner can be challenging. Designing an integrated system for sterilization, surface modification, and packaging can include consideration of the device's application, function, and materials. For example, using heat treatment as a sterilization method can be very cost and time effective. However, one or more components within a medical device may be compromised by the application of temperatures high enough to ensure that pathogens are destroyed.

The specification below describes systems and methods for sterile packaging of surface modified medical devices. These surface modified medical devices may include a range of devices such as electrodes, catheters, RFID tags, and other devices. In one embodiment, the portions of the sterilization process and surface modification process are combined into a single step and packaging is used to simultaneously preserve both the sterility and the surface modification. This results in a cost effective process that reduces the number of steps to produce the final packaged product. Although the illustrative systems and methods described below describe sterilization, surface modification, and packaging of an implantable device having silicone surfaces, the principles described can be applied to a wide range of products.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an example" or similar language means that a particular feature, structure, or characteristic described in connection with the example is included in at least that one example, but not necessarily in other examples.

Figure 1A:
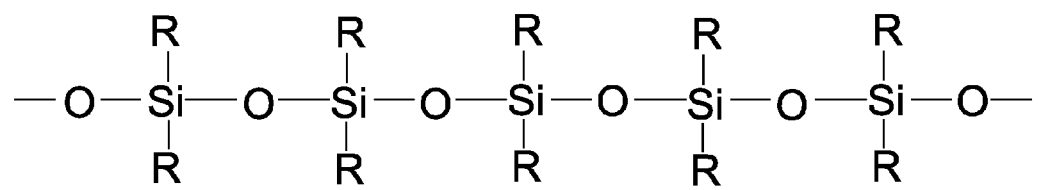
FIGS. 1A and 1B show illustrative chemical structures of silicone, according to one example of principles described herein.
Figure 1B:
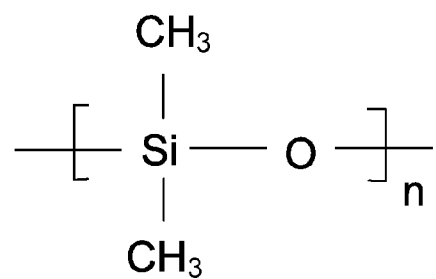

Silicone is a synthetic compound that is used for a variety of purposes, including in implantable devices. As shown in FIG. 1A, silicone is made up of a flexible backbone formed by a chain of alternating silicon (Si) and oxygen atoms (O). Side groups R can be attached on either side of the silicon atoms. The side groups R are not all necessarily identical, but could be any of a variety of different molecules. In one example, FIG. 1B, a methyl group ($CH_3$) is attached on either side of the silicon atoms to form Polydimethylsiloxane (PDMS). Medical grade silicone is chemically inert, biocompatible, and durable in implanted environments. Medical grade silicone can be created with a wide variety of mechanical characteristics. For example, medical grade silicone can be selected to have a hardness ranging from Shore A 10 to 90.

In general, silicone surfaces may be hydrophobic and have a high coefficient of friction. This can lead to a number of challenges when using silicone implanted medical devices. For example, the high coefficient of friction of silicone can make it challenging to slide the implant device through an opening in tissue to the desired position. The mechanical abrasion by the silicone can produce high insertion forces and tissue trauma, which, in turn, may aggravate immune system response to the medical device. Biofilms may also form on the hydrophobic surface of the silicone. Biofilms are a community of cells growing on a solid surface. Biofilms can be of significant concern because of their resistance to immune defenses/antibiotics and can result in subsequent infections. Biological interaction with a silicone surface may also produce an aggravated foreign body reaction to the implant including nonspecific protein absorption, frustrated phagocytosis, and unguided repair. The foreign body reaction results in fibrosis and encapsulation of the implanted device.

The silicone can be modified in a number of ways to change the reaction of the biological tissues to the implanted device. For example, the chemical formulation of the bulk silicone material may be changed. This results in the presentation of a different surface to the biological tissues. However, bulk modification of the silicone can also result in undesirable changes to the mechanical and chemical properties of the silicone.

Another option is to modify the surface of the material to improve biocompatibility without changing its bulk properties. For example, the surface of silicone can be modified by surface activation such as plasma, corona and UV treatment, chemical modification of the surface or by placing a coating over the silicone surface.

Figure 2:
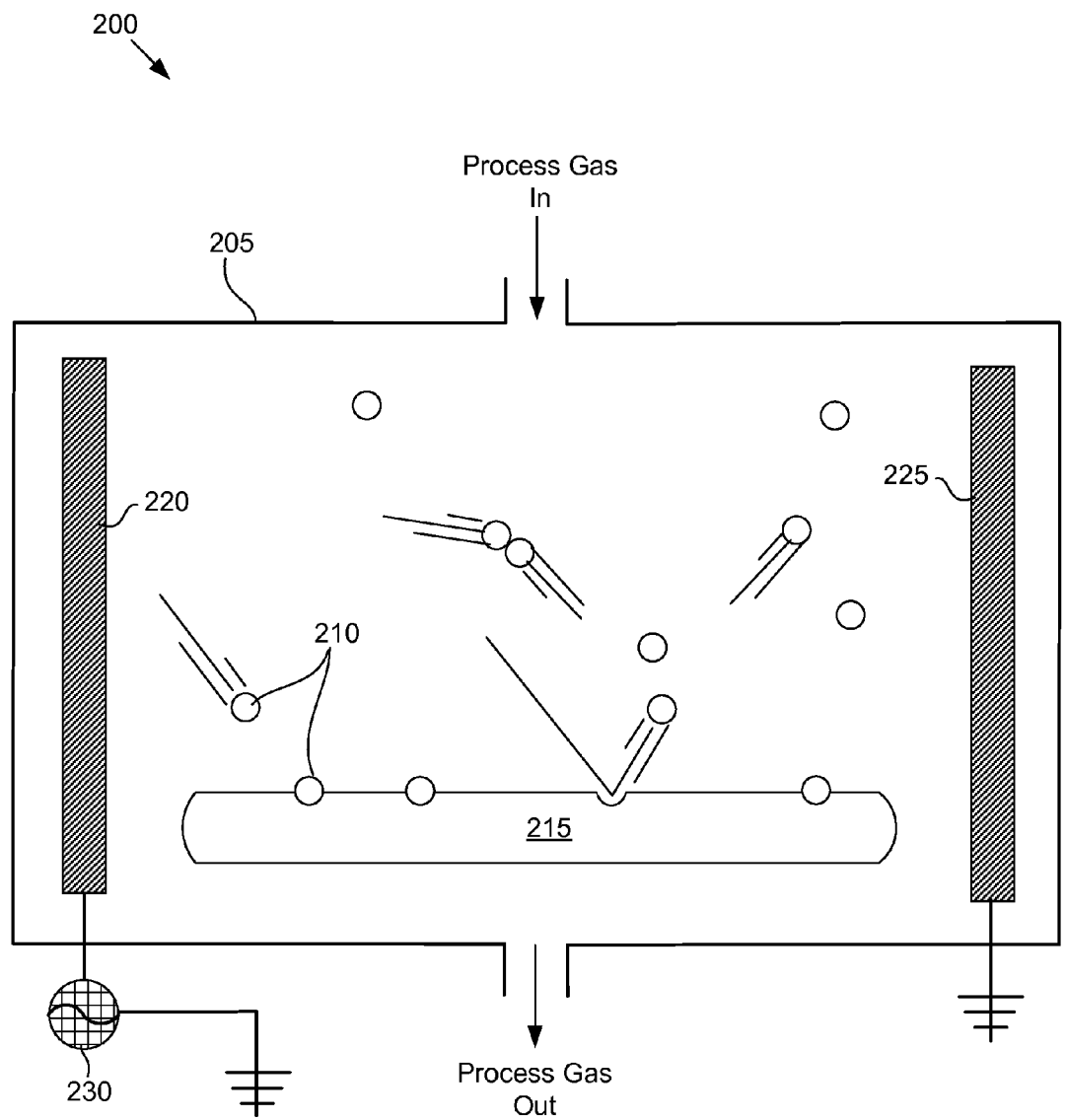
FIG. 2 is diagram of an illustrative system for plasma surface modification, according to one example of principles described herein.

In general, plasma modification of a surface includes exposing the surface to energetic gas molecules in a gas plasma. FIG. 2 is a schematic of plasma surface modification within a plasma reactor (200). The gas plasma may be generated in atmospheric conditions or at a reduced pressure. In one example, glow discharge plasma is created by evacuating a vessel (205) and then refilling it with low pressure process gas (210). The gas plasma (210) is energized using techniques such as radio-frequency energy, microwaves, alternating current, or direct current. A radio frequency source (230) is attached to an excitation electrode (220). A ground electrode (225) on the opposite side of the chamber completes the circuit. The gas plasma (210) may include a variety of energetic species such as electrons, radicals, metastable species, and photons in the short-wave ultraviolet (UV) range. Surfaces in contact with gas plasma (210) are bombarded by these energetic species and the energy of these energetic species is transferred from the plasma to the molecules on the surface. These energy transfers are dissipated within the surface by a variety of chemical and physical processes. This modifies the surface to depths ranging from angstroms to microns without changing the bulk properties of the material. In this example, a polymer surface (215) is exposed to the gas plasma (210).

A wide variety of parameters can directly affect the chemical and physical characteristics of a plasma and subsequently affect the physical and chemical properties of the surface obtained by plasma modification. Processing parameters, such as gas types, treatment power, treatment time, and operating pressure, can be varied by the user. A number of other parameters, such as electrode location, reactor design, gas inlets, and vacuum, are set by the design of the plasma equipment. This wide range of parameters can offer a greater amount of control over the plasma process than most other high-energy radiation processes such as gamma radiation.

These parameters can be selectively controlled to enhance surface wettability and increase the wet lubricity of silicone surfaces. Unfortunately, these silicone surface activation techniques are not permanent and modified surfaces begin to revert back to the original state post plasma treatment. The modified surface recovers its hydrophobic characteristics upon ageing in air, with the largest decay occurring during the first few hours after the surface modification. This instability limits the use of plasma surface activation techniques to an immediate application such as just prior to surgical use or surface modification for the purpose of promoting adhesion right before a coating application. Significant delays, such as extended storage or transportation, can render the plasma surface modification less effective.

There are at least two mechanisms that are theorized to contribute to the reversion of the modified surface to its original state. First, the diffusion of pre-existing low molecular weight silicone fluid from the bulk of the material to the surface can contribute to hydrophobic recovery of the surface. However, medical grade silicones that are designed for long term implantation are specifically manufactured to minimize or eliminate low molecular weight silicone fluid. Consequently, reversion of the modified surface of medical grade silicone due to low molecular weight silicone fluid is not typically significant.

The second mechanism for reversion of the modified silicone surface to its hydrophobic state is backbone chain rotation and surface relaxation. The silicone backbone is very chemically stable. The Si—O bonds are quite polar and without the presence of side groups, the intermolecular interaction between them would be quit high preventing the flexibility of the backbone. However presence of the side groups such as methyl groups which only weakly interact with each other allows for high flexibility of siloxane chain. By rotating the backbone, the silicone surface can revert to a more stable lower energy state by orienting the modified polar side groups of the silicone backbone away from the surface and diffusion of unmodified organic side groups outward from the bulk to the surface. In general, the backbone of silicone adopts a configuration such that the chain exposes the maximum number of organic side groups to the outside and reverts its surface to a more hydrophobic state. The speed with which the silicone surface reverts to a hydrophobic state is influenced by a variety of factors, including ambient temperature and humidity. In some embodiments, these factors may be controlled to slow down the hydrophobic reversion process.

As used in the specification and appended claims the terms "hydrophilic" and "hydrophobic" describe varying amounts of affinity for water or other aqueous solutions. The affinity of a surface for water can be conveniently characterized using the contact angle of water on the surface. Contact angles range between 0 and 180 degrees. Low contact angles indicate that the surface has a hydrophilic attraction to water. The water has a tendency to spread out over the hydrophilic surface. High contact angles indicate that the surface is hydrophobic and tends to repel water. Water has a tendency to bead and run off of hydrophobic surfaces. Thus, decreasing the hydrophobicity refers to making changes to a surface to decrease its contact angle. For example, changes of contact angles from 140 to 95 degrees and 100 to 80 degrees are examples of decreasing hydrophobicity. Untreated medical grade silicones typically have advancing contact angles between 100 and 120 degrees. Plasma treated silicone may have lower contact angles that are dependent on the type of plasma treatment, including the duration of the plasma treatment, the ionic species used, and other factors. For example, plasma treated silicone may have initial contact angles that are between 60 to 80 degrees.

Figure 3A:
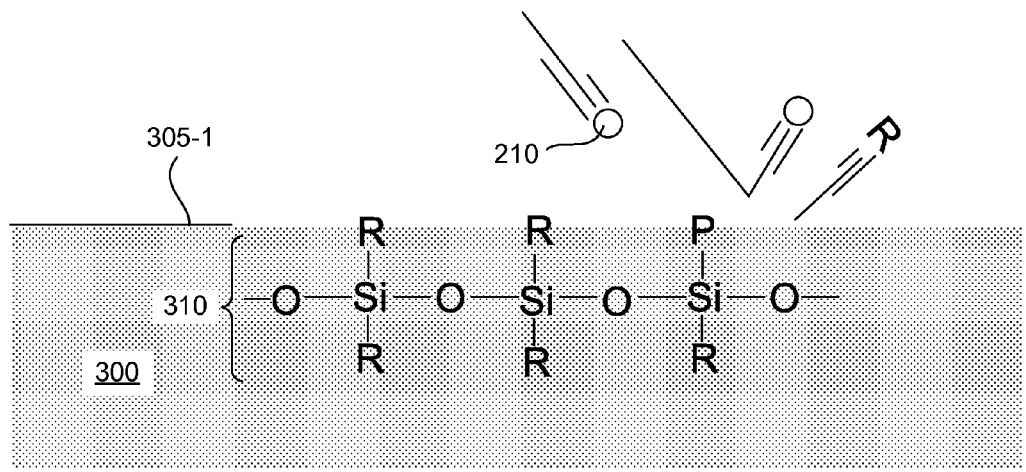
FIG. 3A-3C show modification of silicone molecules at a surface by plasma treatment and subsequent reversion of the surface by backbone rotation, according to one example of principles described herein.
Figure 3B:
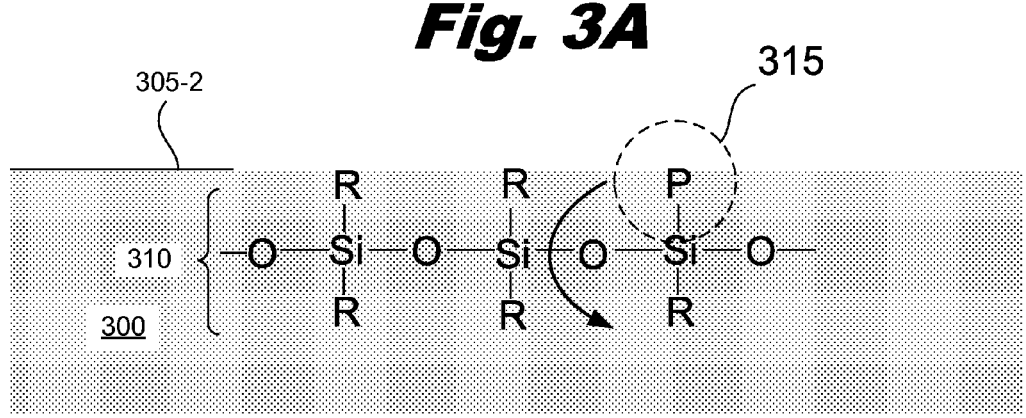

FIGS. 3A-3B are diagrams of a silicone surface. These figures show only a small portion of a silicone molecule and for simplicity do not show adjacent silicone molecules. In FIG. 3A, a silicone body (300) has been placed in a plasma reaction vessel and is bombarded by high energy species in a gas plasma (210). Plasma treatment of the silicone results in changes in chemical and physical characteristic of the surface. For example, the plasma treatment may expose underlying silica filler. The silica filler is polar and increases the hydrophilic nature of the surface (305-1).

The plasma treatment also ejects a portion of the side groups R attached to the backbone of the silicone (310) at the surface (305-1). The ejected side groups are replaced by more polar entities P. The composition of the polar entities may be dependent on the type of plasma used. For example, in the case of oxygen plasma treatment of PDMS the methyl side groups are substituted by more polar entities such as hydroxyl, carbonyl and carboxylic through reaction with O, OH and $O_2$. 3B shows the modified silicone surface (305-2) which has a more hydrophilic nature. However, the siloxane backbone of silicone is highly flexible due to low chain-to-chain interactions and the large distance between the adjacent chains. Therefore, it can easily rotate to present the highest density of the side groups R at the surface.

Figure 3C:
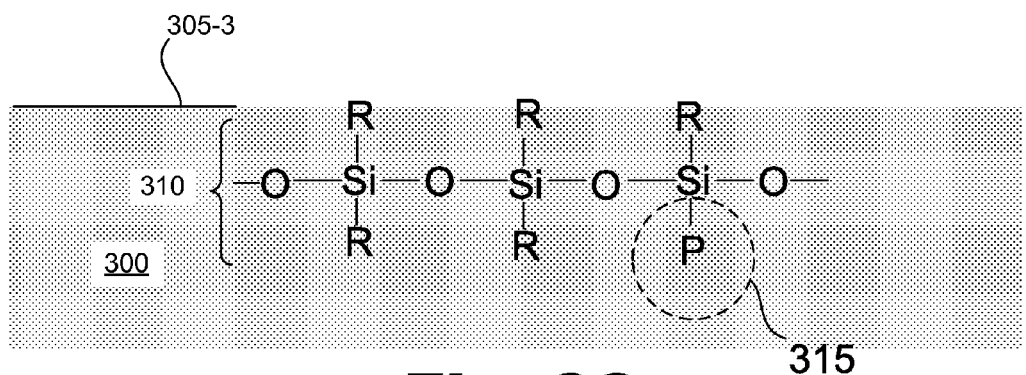

FIG. 3C shows that the backbone rotation of the silicone molecule (310) results in minimization the surface energy and the recovery of the hydrophobic nature of the surface (305-3). As shown in FIG. 3C, the polar groups (315) on the backbone have rotated away from the silicone surface and into the bulk material.

Figure 4:
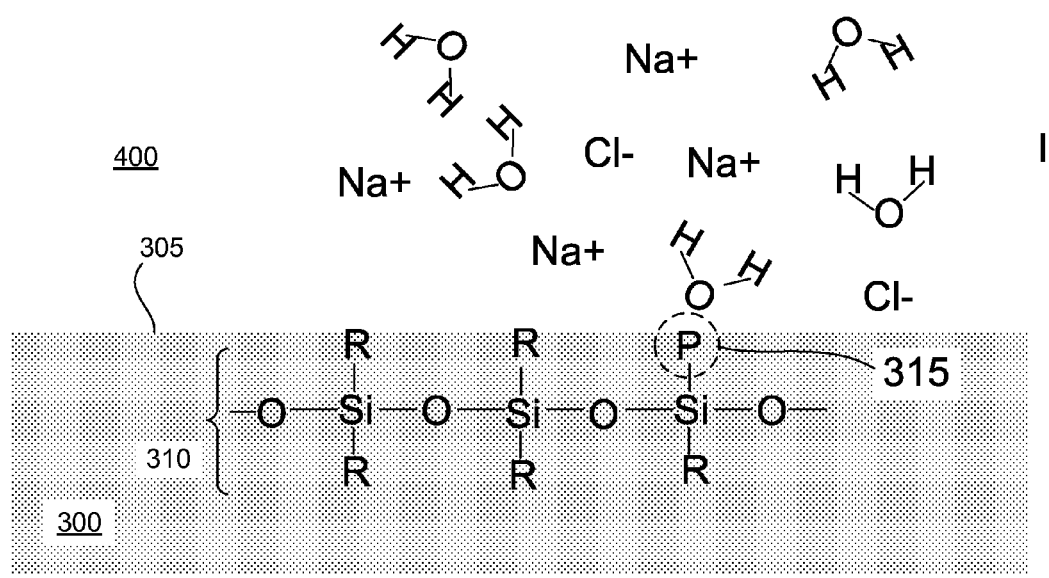
FIG. 4 is a diagram showing preservation of the plasma modified surface using a polar soaking agent, according to one example of principles described herein.

FIG. 4 shows one illustrative method for stabilizing a plasma modified silicone surface (305). In this embodiment, the plasma modified surface (305) is placed in a polar solution (400) before the silicone surface has time for substantial hydrophobic recovery. The polar groups P of the silicone molecules (310) at the silicone surface (305) create a dispersion bond with the molecules in the polar solution (400). This attraction counteracts the tendency of the backbones to rotate and stabilizes the silicone surface (305) as long as the silicone surface (305) is in the polar solution (400). This interaction suppresses further hydrophobic recovery of the modified silicon surface. A variety of polar solutions can be used, including water based solutions such as saline. A number of additives can be added to the polar solution, such as lubricants, bioactive molecules, drugs, or other suitable additives. For example, a water soluble polymer such as polyvinyl alcohol can be added to promote lubricity.

Other surface modification techniques may also be used to increase the hydrophilicity of the silicone and improve its biocompatibility. For example, a coating may be applied to the silicone surface. In some implementations, plasma treatment of the silicone surface may enhance the bond strength between the silicone surface and the coating. In other examples, the silicone surface may be functionalized with hydrophilic molecules.

Figure 5:
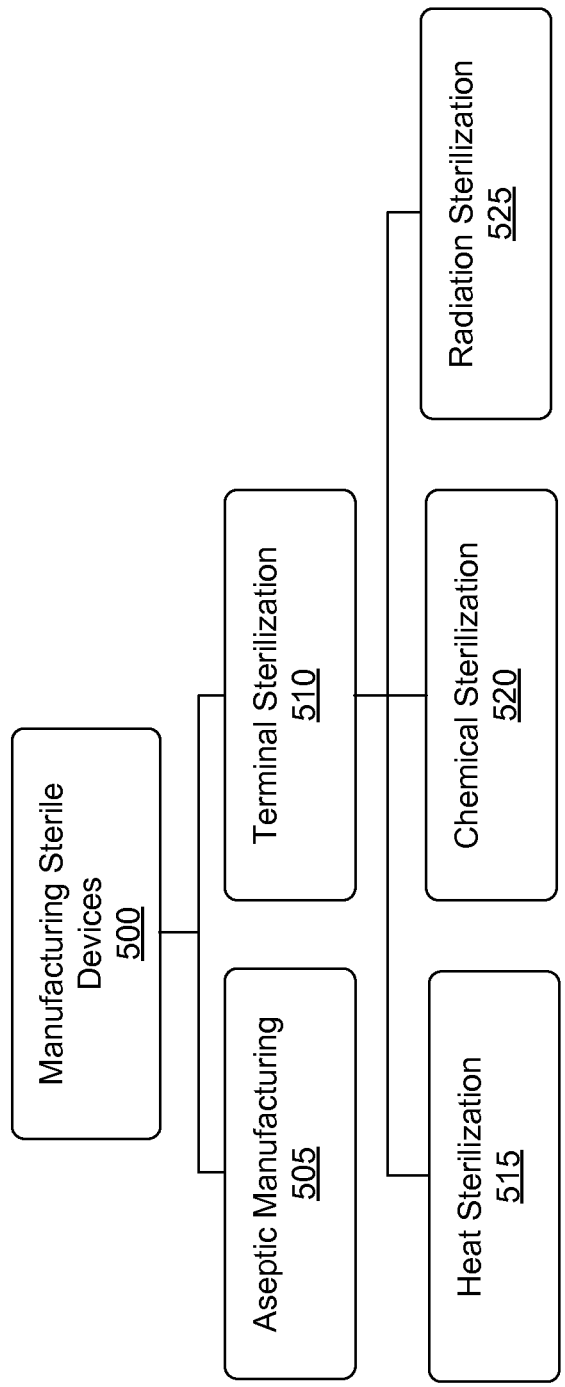
FIG. 5 is a diagram showing various techniques for sterilizing medical devices, according to one example of principles described herein.

To reduce the risk of infection and other complications, medical devices and equipment are sterilized prior to use. FIG. 5 shows a variety of techniques that can be used for manufacturing sterile devices (500), including aseptic manufacturing (505) and terminal sterilization (510). Aseptic manufacturing (505) requires a sterile work environment through all stages of the construction, testing, and packaging of the medical device or equipment. This is complex, expensive, and time consuming. Consequently, many medical device manufactures choose a terminal sterilization technique (510) for post manufacturing sterilization of the device. Terminal sterilization techniques include heat sterilization (515), chemical sterilization (520), and radiation sterilization (525).

Heat sterilization (515) raises the temperature of the medical device, usually in its packaging, to levels that kill any bacteria, microbes, viruses, or other organisms present. For example, the medical devices may be loaded into an autoclave. The autoclave raises the temperature and pressure to kill organisms on the medical devices. However, many implantable devices cannot withstand the high temperatures and pressures used in autoclaving. Heat sterilization may be a less attractive option for cochlear implants or other active medical devices because of the possibility of thermo-mechanical stresses induced in the components of the active medical device due to rising temperature and the coefficient of thermal expansion (CTE) mismatch. Also most of the device packaging materials do not withstand the high temperature and pressure requirements of heat sterilization process.

Chemical sterilization (520) includes techniques that use chemicals, such as ethylene oxide, to kill biological contaminants. Chemical sterilization can be a viable option when it does not interfere with any surface modification which has previously occurred. However, due to safety concerns with the use and stringent disposal requirements of the chemicals used in the sterilization process it is usually outsourced to a specialized partner. This outsourcing not only increases the cost and complexity of the production, but introduces a substantial delay in market delivery.

As discussed above, plasma treatment modifies only the surface of the polymer and allows simultaneous surface modification and sterilization. Plasma sterilization is an environmentally friendly process with minimal waste that can be done in house (point of manufacturing sterilization), eliminating vendor dependency as well as the cost and complexity of planning associated with contract sterilization. It is important however to consider that if the surface of the device is already modified, for example by ways of surface functionalization, then the plasma sterilization can be detrimental to the modified surface and should not be used.

Radiation sterilization (525), such as gamma radiation, can be used to sterilize devices and packaging. However, high doses of radiation can change the material properties of polymers used in the device and packaging. High dose radiation can have adverse effects on the molecular structure of the polymers used in the device. For example, high dose gamma radiation can cause changes in physical/mechanical properties of the polymer such as hardness and tear resistance. This change in bulk characteristics is attributable to the polymer chain scission, crosslinking, and increased polymer-filler interfacial interactions. However, low dose gamma radiation sterilization (525) can be considered in combination with other sterilization techniques and aseptic manufacturing.

Another radiation based technique is plasma sterilization. Plasma sterilization is not only effective in killing highly resistive bacteria but also capable of eliminating pyrogens (fever-inducing residues of fungi or bacteria) by degrading cell residues and compounds. Plasma sterilization can be used to simultaneously modify a silicone surface to be more hydrophilic while sterilizing the medical device. This provides a significant advantage by combining two processes into a single, effective treatment. The combined plasma treatment simplifies the production process and decreases the likelihood of subsequent contamination. As mentioned above, the surface modification produced by plasma treatment spontaneously reverts back to a more hydrophobic state. The description below describes illustrative packaging methods that preserve hydrophilic nature of the silicone surface generated by the plasma treatment.

Figure 6A:
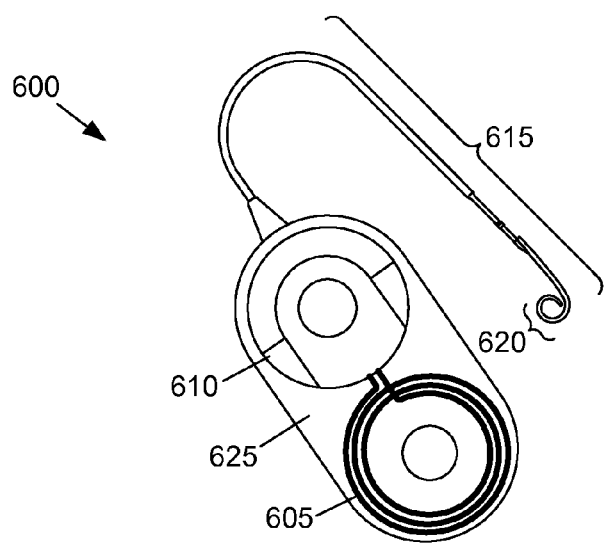
FIG. 6A is top view of an illustrative implantable device, according to one example of principles described herein.
Figure 6B:
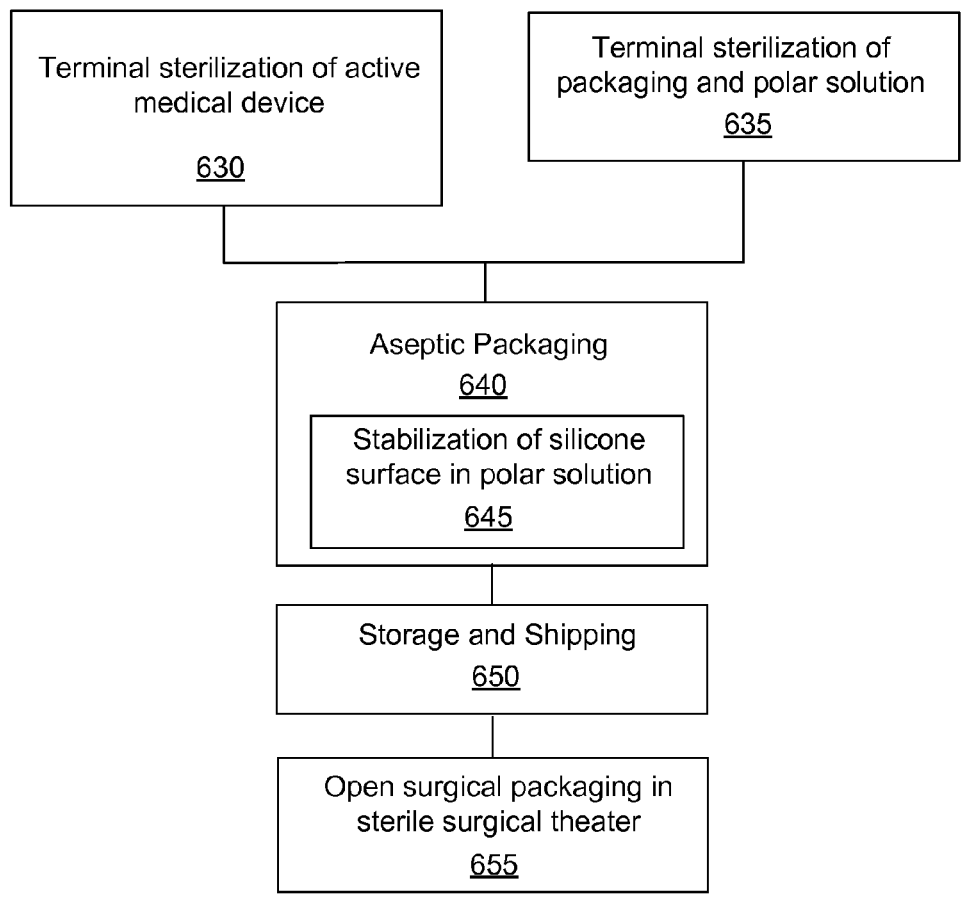
FIG. 6B is an illustrative method for sterile packaging of surface modified implantable devices, according to one example of principles described herein.

FIGS. 6A and 6B provide an illustrative example of sterile packaging for a surface modified implantable device. FIG. 6A is a top view of a cochlear implant, which is one type of implantable device (600). This illustrative implantable device (600) includes an internal processor (610), an antenna (605), and a cochlear lead (615) having an electrode array (620). The implantable device (600) is surgically implanted such that the electrode array (620) is internal to the cochlea. The internal processor (610) and antenna (605) are secured beneath the user's skin, typically above and behind the external ear, with the cochlear lead (615) connecting the internal processor (610) to the electrode array (620) within the cochlea. The antenna (605) receives signals from an external transmitter and sends the signals to the internal processor (610). The internal processor (610) modifies the signals and passes them along the appropriate wires to activate one or more of the electrodes within the electrode array (620). This provides the user with direct sensory input that is a representation of external sound waves.

Medical grade silicone (625) is used to encapsulate the entire implantable device (600), with the exception of the exposed electrodes or optical windows. For example, after the implantable device (600) has been assembled and electrical connections are made, the device could be fully or selectively covered by a medical grade silicone. Thus, a significant portion of the exterior of the implantable device (600) is a silicone surface. The process of encapsulating the implantable device (600) in silicone may occur all at once or piecewise. For example, the silicone may be deposited over the device by extrusion, molding or a combination process.

FIG. 6B describes an illustrative method for sterile packaging of a surface modified cochlear implant. After manufacturing, the device is terminally sterilized with the goal of eliminating pathogens on the surface of the device. As shown in FIG. 6B the cochlear implant is simultaneously terminally sterilized and surface modified by exposure to plasma gases (block 630). The plasma sterilization is not only effective in killing highly resistive bacteria but also is capable of eliminating pyrogens (e.g. fever-inducing residues of fungi or bacteria) by degrading bacterial cell residues and compounds. It at the same time modifies the surface of the device and by increasing hydrophilicity of the silicone improves its wet lubricity.

The polar solution and packaging are also terminally sterilized (block 635). A wide variety of techniques can be used, including inexpensive and straightforward techniques such as autoclaving both the solution and the packaging.

Aseptic packaging is performed by placing the device into the polar soaking solution in an aseptic environment (block 640). The silicone surface is stabilized through interaction with the polar solution (block 645). The polar groups present at the surface of the oxidized silicone create a dispersion (van der Waals interaction) bonding to the molecules of the polar solution such as deionized (DI) water/phosphate buffered saline (PBS). This prevents backbone rotation and migration of the low molecular weight entity to the surface and consequent hydrophobic recovery. In other embodiments, molecules of the additives in the solution may be adsorbed to the modified surface or even covalently bonded to the modified surface. As used in the specification and appended claims, the term "bind" refers to both adsorption (physisorbed) and chemical bonding (chemisorbed) of molecules. The surface modified device is placed in the polar solution and packaging before substantial hydrophobic reversion of the silicone surface occurs. For example, the surface modified device may be placed in the polar solution within three hours of surface modification. Preferably, the device would be placed in the polar solution within one hour after surface modification and more preferably the device would be placed in the polar soaking solution immediately after surface modification. In some examples, the device may be cooled or placed in an interim polar solution if it cannot be placed in the polar solution and packaging within a desired time frame.

The polar solution can include other ingredients to promote additional functionalities. For example, lubricants, bioactive molecules, and drugs may be added to the polar solution. The additives may be natural or synthetic lubricants. In one implementation, a biocompatible water soluble polymer such as polyvinyl alcohol (PVA) can be added to further promote lubricity. Additionally or alternatively, the additive may be a natural polymer such as hyaluronic acid.

Placing the medical device in the polar solution results in stabilization of the plasma modified surface through interactions with the polar solution. Thus, the plasma modified surface is prevented from reverting to its previous hydrophobic state.

The implantable device is stored and shipped to a desired location for surgical implantation (block 650). The sterile package is opened in a sterile surgical theater a short time before the actual implantation of the implantable device in the patient (block 655).

The method in FIG. 6B is only one example. The method may be altered in a number of ways, including deleting, adding, or combining blocks. For example, an additional block could be added following block 640, in which the completed package is subjected to low dose gamma radiation to further ensure the sterility of the final packaged product. Additionally, the polar solution or other surface stabilization material may be deposited on the modified surface in a number of ways, such as dipping, spraying, or other suitable deposition technique.

FIG. 7 is a cross sectional view of the cochlear implant in its final packaging (700). In this example, the packaging includes a shaped polymer boat (710) which contains the polar solution (715). After the appropriate sterilization of the packaging, polar solution, and cochlear implant, the cochlear implant (600) is submerged in the polar solution (715). This can occur in a variety of ways, including putting the solution in the package, sterilizing the solution and package together and then adding the sterilized cochlear implant. Alternatively, sterilization of the solution and package could be performed separately, and then the sterilized solution can be placed in the sterilized package and sterilized cochlear implant submerged in the sterilized solution. In another implementation, the sterilized cochlear implant may be first placed in the sterilized package and then the sterilized solution added.

A cover (705) is sealed over the top of the polymer boat (710). The cover (705) and the polymer boat (710) seal the solution (715) and cochlear implant (600) from exterior contamination and prevent leakage of the solution from the package. According to one illustrative embodiment, the packaging process is performed so that minimal bubbles are trapped in the polar soaking solution (715).

This packaging method provides a number of advantages. As discussed above, the polar solution maintains the hydrophilic nature of the silicone surface and increases the lubricity of the cochlear lead. This can facilitate insertion of the electrode array into the cochlea, reducing the insertion forces and result in reduced tissue trauma during insertion and consequently preserve patients' residual hearing.

This packaging method provides other advantages during the surgical procedure. By packaging and shipping the cochlear implant immersed in a polar solution such as PBS functionality of the device can be confirmed in the operating room. In some embodiment tests may be performed while the cochlear implant is still encased in the packaging. Tests that can be performed while the cochlear implant is still in its package may include testing the functionality of the electrodes and electronics by wirelessly transferring power and signals to the cochlear implant through the packaging. Additionally or alternatively, a plug may be designed in the package for communication of the test equipment with the cochlear implant. For example, electrical field imaging (EFI) techniques can be used to test the processor functions and the resistivity of the individual electrodes. This and other tests can be used to ensure that the cochlear implant is functional prior to opening the package.

In conclusion, plasma gas can be used to simultaneously modify the surface chemistry and clean/sterilize polymer surfaces of implantable devices and the hydrophobic recovery of the silicone can be prevented by aging in solution.

The preceding description has been presented only to illustrate and describe examples of the principles described. This description is not intended to be exhaustive or to limit these principles to any precise form disclosed. Many modifications and variations are possible in light of the above teaching.

What is claimed is:

1. A system comprising:
    a cochlear implant comprising a sterilized hydrophilic silicone outer surface;
    a polar solution, the cochlear implant immersed in the polar solution; and
    sterile packaging enclosing the polar solution and cochlear implant.

2. The system of claim 1, in which molecules in the polar solution bond with polar groups on silicone molecules by physisorbed bonding to prevent backbone rotation of the silicone molecules.

3. A method for sterile packaging the system of claim 1, the method comprising:
    irradiating the silicone outer surface of the cochlear implant such that the surface is simultaneously sterilized and hydrophobicity of the surface is decreased;
    covering the surface in the polar solution to suppress hydrophobic recovery of the surface; and
    enclosing the polar solution and cochlear implant in the sterile packaging.

4. The method of claim 3, further comprising sterilizing the polar solution using terminal sterilization to form the sterile polar solution.

5. The method of claim 3, further comprising:
    sealing the sterile packaging, and
    transporting the sealed packaging to an operating theater.

6. The method of claim 3, in which the surface comprises a medical grade silicone.

7. The method of claim 3, in which the implant comprises components with varying coefficients of thermal expansion.

8. The method of claim 3, in which the implant comprises active components.

9. The method of claim 3, in which irradiating the surface comprises:
    placing the implant in a plasma chamber;
    energizing low pressure process gas to create a plasma; and
    exposing the implant to the plasma for a predetermined period of time.

10. The method of claim 3, in which the polar solution comprises water, sodium chloride, and polyvinyl alcohol.

11. The method of claim 9, in which plasma irradiating the silicone outer surface comprises using oxygen as a process gas in the plasma chamber, the oxygen creating hydroxyl functionality that decreases the hydrophobic nature of the silicon surface.

12. The method of claim 9, further comprising depositing a coating on the silicone outer surface prior to plasma treatment, in which molecules in the coating are crosslinked onto the silicone outer surface.

13. The method of claim 9, in which plasma irradiating the silicone outer surface comprises forming a hard skin on the surface of the silicone outer surface less than 10 μm in depth.

14. The method of claim 3, further comprising sterilizing the polar solution and packaging using heat treatment in an autoclave.

15. A method for sterile packaging the system of claim 1, the method comprising:
    selecting a treatment time and treatment power of a plasma chamber such that energetic species in a gas plasma impact the silicone outer surface of the implant and create polar groups in silicone molecules near the surface, the hydrophobic nature of the surface being decreased; and
    before significant hydrophobic recovery occurs, submerging the silicone outer surface in the polar solution.

16. The method of claim 15, in which the polar solution comprises water and polyvinyl alcohol.

17. The method of claim 15, in which the polar solution comprises water and hyaluronic acid.

18. The method of claim 15, further comprising aseptically packaging the implant and polar solution in an aseptic environment.

19. The method of claim 15, in which backbone rotation of silicone molecules at the silicone surface is suppressed by physisorbed bonding between the silicone molecules and the polar solution.

20. The method of claim 15, further comprising sterilizing the polar solution and a package, the polar solution contained in the package, prior to submerging the silicone outer surface in the polar solution.

21. The method of claim 15, further comprising separately sterilizing a polar solution and a package; in which submerging the silicone outer surface in the polar solution comprises placing the sterilized polar solution in the sterilized package and then placing the implant in the sterilized polar solution.

22. The method of claim 15, in which submerging the silicone outer surface in the polar solution comprises placing the implant in the sterile packaging and then adding the sterile polar solution to the packaging.

23. The method of claim 15, further comprising electrically testing the implant while the device is submerged in the sterile polar solution.

* * * * *